United States Patent [19]
Huetter et al.

[11] Patent Number: 5,788,373
[45] Date of Patent: Aug. 4, 1998

[54] METHOD AND APPARATUS FOR PERFORMING SINGLE DIFFERENTIAL THERMAL ANALYSIS

[75] Inventors: Thomas Huetter, Niederrohrdorf; Urs Joerimann, Bertschikon; Hans-Georg Wiedemann, Staefa, all of Switzerland

[73] Assignee: Mettler-Toledo GmbH, Greifensee, Switzerland

[21] Appl. No.: 649,181

[22] Filed: May 17, 1996

[30] Foreign Application Priority Data

May 19, 1995 [CH] Switzerland .................... 1491/95

[51] Int. Cl.⁶ .................................................. G01N 25/00
[52] U.S. Cl. .................................... 374/10; 374/43
[58] Field of Search .............................. 374/10, 11, 12, 374/13, 14, 43, 44, 45, 46, 47, 48, 49, 50, 51, 52; 364/557

[56] References Cited

U.S. PATENT DOCUMENTS

| | | | |
|---|---|---|---|
| 3,028,754 | 4/1962 | Huyser | 374/46 |
| 3,283,560 | 11/1966 | Harden et al. | 374/12 |
| 3,344,654 | 10/1967 | Erdey et al. | 374/14 |
| 4,154,085 | 5/1979 | Hentze | 374/10 |
| 4,354,764 | 10/1982 | Achermann et al. | 374/56 |
| 4,812,051 | 3/1989 | Paulik et al. | 374/10 |
| 4,848,921 | 7/1989 | Kunze | 374/11 |
| 5,165,792 | 11/1992 | Crowe et al. | 374/10 |
| 5,211,477 | 5/1993 | Li | 374/10 |
| 5,288,147 | 2/1994 | Schaefer et al. | 374/10 |
| 5,370,457 | 12/1994 | Iizuka | 374/51 |
| 5,549,387 | 8/1996 | Schawe et al. | 374/10 |

OTHER PUBLICATIONS

Hemminger, W.F., H.K. Cammenga, "Methoden der Termischen Analyse" [Methods of Thermal Analysis]. Springer Publishers 1989, from the series entitled Guidelines for Chemical Laboratory Practice.

*Primary Examiner*—G. Bradley Bennett
*Attorney, Agent, or Firm*—Laubscher & Laubscher

[57] ABSTRACT

A method and apparatus for performing single differential thermal analysis of a sample relative to a reference, using either one reference measurement for a sequence of material measurements—whereby the reference can also be represented by an empty weighing pan—or by the use of a mathmematical model which is so determined that it takes the real behavior of the thermal analytical apparatus into account. Reference temperature curves are generated relative to time of an empty furnace or a reference sample contained in the furnace, and temperature curves of a sample to be measured are taken at the exact same location in the furnace. The reference and sample temperature curves are compared to determine the temperature difference. The reference temperature curve can be calculated mathematically from the measured furnace temperature and the heat transmission factor between the furnace temperature and the temperature of the location of the sample in the furnace, whereby it is possible to determine the differential thermal analysis by a single measurement.

9 Claims, 3 Drawing Sheets

METHOD AND APPARATUS FOR PERFORMING SINGLE DIFFERENTIAL THERMAL ANALYSIS

BACKGROUND OF THE INVENTION

1. Field of the Invention

This invention relates to a method and apparatus for performing single differential thermal analysis of a sample relative to a reference, either by the use of one reference measurement for a sequence of material measurements—whereby the reference can also be represented by an empty weighing pan—or by the use of a mathematical model which is so determined that it takes the real behavior of the thermal analytical apparatus into consideration.

2. Brief Description of the Prior Art

In the case of differential thermal analyses, for example, the temperature is regulated, raised, lowered, or kept isothermal in a furnace. In addition to the sample to be measured, the furnace contains a reference or comparison sample whose temperature behavior is known. The material of the reference sample as a rule does not contain any anomalies in the temperature measurement that is of interest here. Above all aluminum oxide or the empty sample pan or receptacle is customary and suitable for use as a reference material. The difference derived from the sample temperature and the reference temperature is a measure of the heat flow change of the sample. The technique of thermal analyses, especially also the technique of differential thermal analyses and dilatometric analysis techniques, is described in a comprehensive fashion in the text book entitled "Methoden der Thermischen Analyse" [Methods of Thermal Analysis], W. F. Hemminger, H. K. Cammenga, Springer Publishers 1989, from the series entitled "Guidelines for Chemical Laboratory Practice"; the content of this text book is thus included by reference in the instant specification.

If the reference sample and the sample to be measured are simultaneously placed in the furnace then —even in case of the best analysis instruments, made with maximum precision—there are certain nonhomogeneities and differences not only in the heat and temperature fields but also in the material of those instruments themselves. The reference sample and the sample to be measured are located in different places in the furnace; in other words, they are exposed to a non-completely homogeneous temperature field in different places.

Moreover, the reference sample and the sample to be measured influence each other. That is a disturbing factor above all because this influences greatest, of all things, in the particular interesting temperature range or time frame, where the sample to be measured, on the basis of the exothermal of endothermal processes, shows deviations in the sample to be measured from the reference sample.

The sample carrier, for example, the pan carrier or the pan itself, not only for the reference and for the sample to be measured, but also the measurement sensors themselves, always show minor differences. This leads to small although always disturbing influences on the measurement results and adulterations of the results.

If an analysis apparatus is to be used to determine not only a single material property but also various different material properties, in other words, if, in addition to differential thermal analysis, for example, one also determines dilatometric properties, in other words, if one performs a thermal-mechanical analysis (TMA) or a dynamic-mechanical analysis (DMA) of the sample to be measured, then the result of the differential thermal analysis can be additionally influenced in a negative manner by the expanded measurement arrangement for the determination of these additional material properties in the sample to be measured.

SUMMARY OF THE INVENTION

Accordingly, a primary object of the present invention is to provide an improved differential thermal analysis method and apparatus which avoids the above and other drawbacks of the prior art, characterized in that the temperature behavior of the reference sample and of the sample to be measured are determined at exactly the same spot in the heat and temperature fields of the furnace. The heating and temperature measurement probe are identical for the reference sample and the sample to be measured.

According to a more specific object of the invention, during the differential thermal analysis method, use is made either by one reference measurement for a sequence of material measurements—whereby the reference can also be represented by an empty pan—or by the use of a mathematical model, which is so determined that it takes the real behavior of the thermal analytical apparatus into consideration. In other words, the use of a reference sample material as such can be avoided. In keeping with the designations of the individual processes, that are known as of now in thermal analysis, this new differential thermal analysis is identified by the name of "Single Differential Thermal Analysis (SDTA)."

BRIEF DESCRIPTION OF THE DRAWINGS

Other objects and advantages of the invention will become apparent from a study of the following specification, when viewed in light of the accompanying drawings, in which.

DETAILED DESCRIPTION

Figure 1:
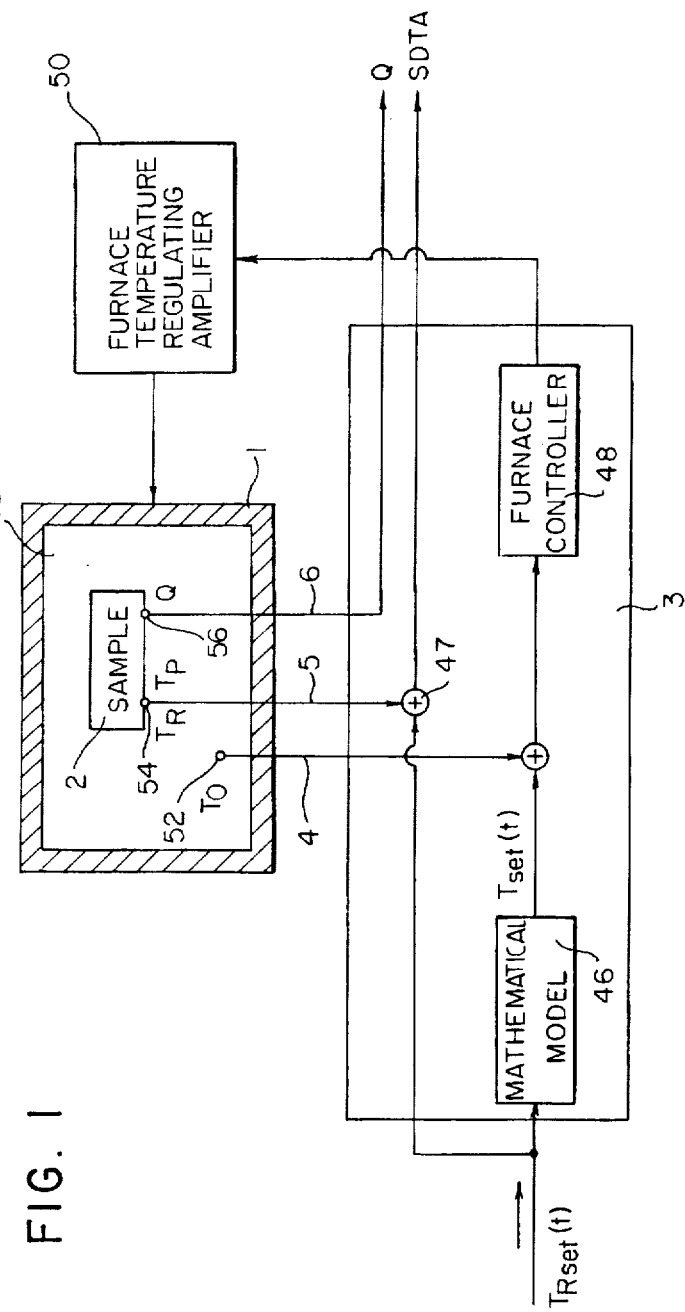
FIG. 1 is a diagrammatic illustration of the apparatus for practicing the present invention.

Referring first more particularly to FIG. 1, the furnace 1 contains a chamber 10 for receiving the sample to be measured 2. The temperature $T_o$ of furnace 1 can be regulated in an altered fashion by means of a heating unit and/or cooling unit 50 according to predetermined rules, that is to say, it can be raised or lowered, or it can also be kept constant. The heating or cooling of the furnace 1 can be controlled, for example, by computer means 3.

The furnace temperature $T_o$ is measured with one or several sensors 52 and the electrical signals, corresponding to the measured values, are transferred to computer 3 via line 4 for combination with the signal $T_{set}$ (t), as will be described below.

The temperature $T_p$ of sample 2 which is to be measured and/or of the sample carrier, is measured with one or several sensors 54 and the electrical signals, corresponding to the measured values, are transmitted to computer 3 via line or lines 5.

Using line or lines 6, additional values Q, measured on sample 2—for instance, mass changes, such as changes in length, electrical properties, such as the dielectrical constant, magnetic properties, optical properties, elastic properties—are detected by sensor means 56 and are transmitted via line 6 to computer 3 as electrical signals and are further processed there. Conversely, the computer is also in a position to control and/or regulate the measurement and the stress devices for the various investigations on sample 2. Here it is possible, in addition to simple differential thermal analysis, simultaneously to determine at least one additional physical property of the sample to be measured.

There are typical technical terms also for the other thermal analysis processes that can be combined with single differential thermal analysis, such as:

DEA/DiElectric Analysis

TOA/Thermo Optical Analysis

For a certain furnace, between the measured temperature $T_o$ in the furnace 4 and in the temperature $T_R$ at the place of the sample, there is a reproducible characteristic difference that depends on the temperature program and the transmission function of the regulating circuit. This characteristic dependence can be described with a mathematical model 46.

With the known mathematical model 46 it is possible to calculate the required set point value $T_{set}(t)$ for the controller 48 from the desired setpoint temperature $T_{R\,set}(t)$ in such a way that the resulting temperature program $T_R(t)$ at the place of the sample in the furnace reaches exactly the desired temperature.

The controlling variable is the furnace temperature $T_o(t)$. The influence from the temperature changes of the sample is negligible. The temperature at the place of the sample $T_R(t)$ is thus set independently of the temperature changes of the sample $T_p(t)$ as if no sample were present. $T_R(t)$ is called the reference temperature.

The difference between the measured sample temperature at $T_p(t)$ and the reference temperature $T_{R\,set}(t)$ is the SDTA signal. It is a measure of the heat flow change of the sample.

In the special case of a constant heating or cooling rate, we illustrate, below, a possible mathematical model and a process for determining it.

If the cooling or heating rate $dT_R/dt$ is constant, then, for a certain temperature T, the difference from the furnace temperature $T_o$ and the temperature at the place of the sample $T_R$ is proportional to the cooling or heating rate $dT_R/dt$:

$$T_o - T_R = \gamma(T) \cdot dT_R/dt$$

The proportionality factor $\gamma(T)$ is a time constant. It results from the heat capacity of the crucible and the sample, and the heat resistance between the temperature measurement points for temperature $T_R$ at the place of the sample and for temperature $T_o$ in the furnace.

Figure 4:
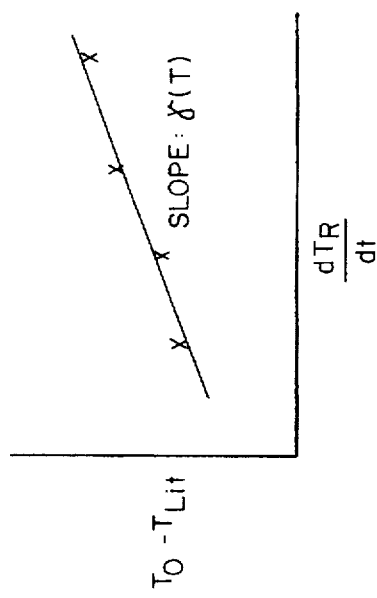
FIG. 4 shows the measurement for the determination of the time constant.

For a certain temperature, the time constant $\gamma$ can for example be so determined that the unknown conversion point of a sample is measured for at least two heating rates. If one graphically plots the difference between furnace temperature $T_o$ and the known conversion temperature $T_{Lit}$ graphically against the heating or cooling rate, then the slope of the straight line is the desired time constant $\gamma$ for this temperature. (see PTB - Mitteilung 1001/90, "Die Temperaturkalibrierung dynamischer Kalorimeter" ("Temperature Calibration of Dynamic Calorimeters," by Huhne, Camenga et al). FIG. 4 illustrates the method for determining the time constant.

The temperature dependence of the desired time constant $\gamma(T)$ for example can be determined by determining it for several reference samples with known conversion points. The melting points of pure metals, for example, are suitable for determining the time constant, for instance:

Indium (In) with a melting point of 156.6° C.

Zinc (ZN) with a melting point of 419.5° C.

Aluminum (Al) with a melting point of 660.3° C.

Gold (Au) with a melting point of 1,064.2° C.

The temperature dependence can then for example be described by a regression of a polynomial of the second order:

$$\gamma(T) = a + b \cdot T + c \cdot T^2$$

If the mass of the reference sample is small enough, one may assume that the reference sample does not change the temperature at the place of the sample.

In other words, by means of the mathematical model and the measured temperature, it is possible, in the furnace, so to control the temperature at the spot of the sample that the desired, arbitrary temperature program will be attained. The difference between the measured sample temperature $T_p$ and the reference temperature determined by means of the mathematical model is a measure of the heat flow change of the sample (DTA-Signal).

Figure 5:
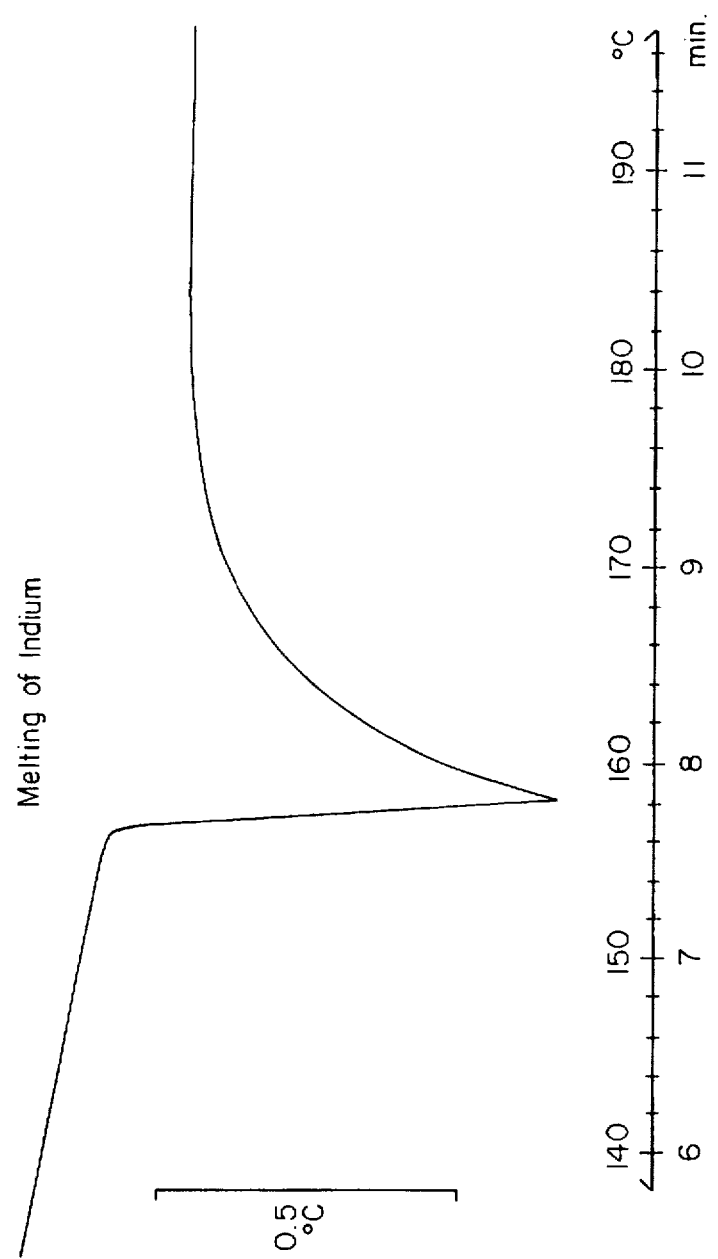
FIG. 5 is a graphic illustration of the differential temperature curve of a given example.

If the difference between temperature Tp of the sample and the required setpoint temperature T, over a span of time, is calculated and illustrated graphically for a given heating rate, then the difference is extensively constant, in other words, the values are located along a straight line that runs parallel to the time axis. That applies so long as there is no anomaly. The moment an anomaly occurs in a certain sample at a certain temperature, the difference becomes greater or smaller, as illustrated in FIG. 5.

In single differential thermal analysis, the temperature curves—measured in succession in terms of time—of a reference sample or of the empty furnace—which can also be used as a reference—and of a sample 2 to be measured are measured on the same spot and are compared to each other. One can also use a mathematically determined temperature curve as reference temperature curve. If, for a certain configuration of the measurement setup, the temperature curve of the reference sample or that of the furnace or a temperature curve derived mathematically from the temperature curve of the reference sample or the furnace has been determined, then, using one singular measurement, each time, one can, in a simple fashion, and on the sample to be measured, determine the thermal-analytical properties and the values of samples to be measured.

Conversely, it is naturally also possible first of all to determine the values of the sample to be measured or of the several samples to be measured and subsequently to determine the temperature curve of the reference sample or that of the furnace or a temperature curve subsequently derived mathematically from the temperature curve of the reference sample or of the furnace—something that is just as simple.

Simultaneously with the measurement of material sample 2 which is to be measured for differential thermoanalysis, one can determine additional physical properties of that sample 2 as a function of the temperature Tp of the sample (simultaneous thermoanalysis). In combination with thermomechanical analysis, it is thus possible to measure changes of length in one direction or changes of volume in several directions, preferably, in a rectangular coordinate system. In this kind of combination thermoanalysis one can furthermore use not just one constant load but one can also apply the load according to a function that is changeable in terms of time. In this kind of dynamic stress, one can, in addition to the static dimension change, also observe a phase shift in terms of time that permits further statements as to material properties. In case of a periodic excitation, for example, with a sinusoidal load, one can, by means of a frequency analysis, particularly, with the help of a Fourier analysis, characterize the behavior of the material. Such dynamic excitations and the attendant analysis methods are known in other technical disciplines, such as control engineering, described in detail, for example, in the textbook entitled "Identifikation dynamischer Systeme" [Identification of Dynamic Systems], Rolf Isermann, Springer Publishers, 1988. As is the case with thermomechanical analysis, differential thermoanalysis can also be combined by measuring the curve of the dielectricity constant. The measurement of the dielectricity constant is described in the technical text entitled "Werkstoffe der Elektrotechnik" [Raw Materials of Electrical Engineering], Hans Fisher, Hanser Publishers, 1982, Pages 324 ff.

Furthermore, differential thermoanalysis can be combined with the measurement of the course of optical properties of materials. Such thermoanalytical optical processes are defined in the already introduced textbook "Methoden der Thermischen Analyse" [Methods of Thermal Analysis], on page 214. That textbook also comprehensively covers the further development of differential thermoanalysis into Differential Scanning Calorimetry (pages 5 ff).

Figure 2:
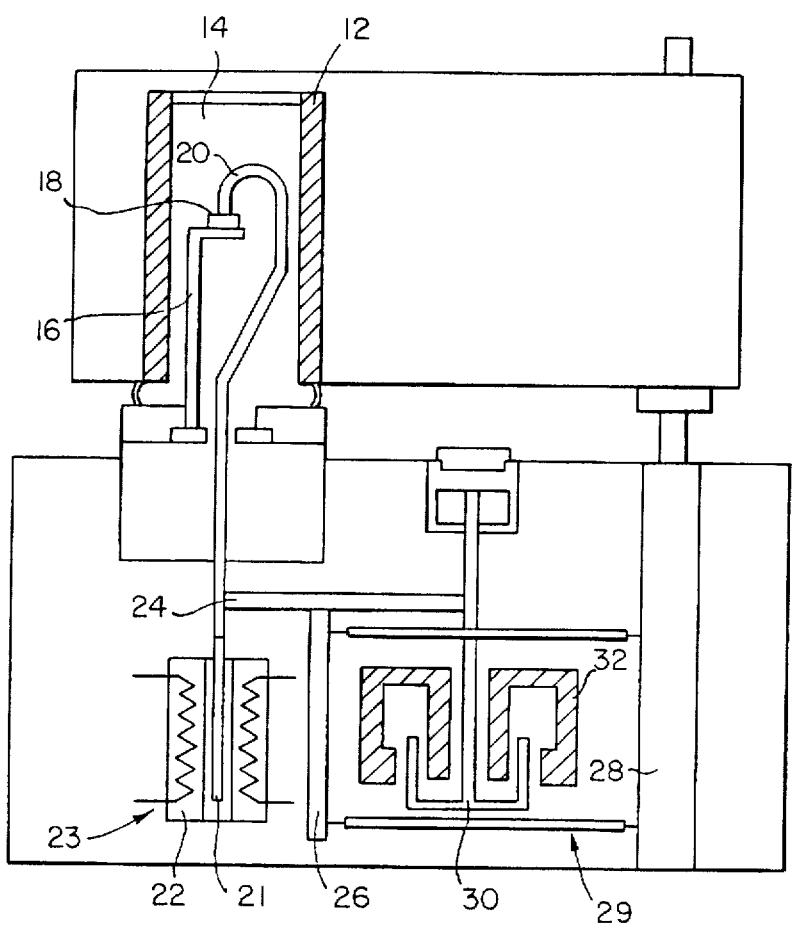
FIG. 2 is a diagrammatic view of a preferred embodiment for practicing the invention.

Referring to FIG. 2, a preferred embodiment is illustrated that is suitable for differential thermal analysis combined with the thermal-mechanical analysis according to the invention. This instrument has a furnace 12 in whose inner chamber 14 is mounted a sample carrier 16. A sample 18 can be placed in this sample carrier. Furnace 12 and sample carrier 16 have the same facilities for temperature control and temperature measurement as was explained earlier in connection with FIG. 1 which, however, are not shown in this schematic illustration. Additionally, this instrument in FIG. 2 shows a measurement device that is able to determine the vertical length change of the sample. This device comprises a measurement strap 20 which, at one end, rests on sample 18 and, at its other end extends within a coil 22 to form a differential transformer 23 for measuring the shifting motion of measurement strap 20, thereby to determine the dimensional change of sample 18. The second end of measurement strap 20, which extends within the coil, is made as a magnetic core 21 and is fashioned of a material that has suitable magnetic properties in order to ensure the function of the differential transformer. In order precisely to control measurement strap 20, the latter is connected, via connecting element 24, with parallel guide means 26 that is supported by the housing 28. The inherent weight of this measurement means device, consisting of measurement strap 20 and parallel guide means 26, is not negligibly small so that it can influence the measurement results. This is why, attached to the parallel guide 26, there is provided electromagnetic load compensation means 29 that comprises a coil 30 and a magnetic circuit 32 and that works according to the known plunger coil principle, in which, by regulating the current through coil 30, one can adjust the magnitude of the compensation force to the desired magnitude. Such a known compensation device is described in the Achermann et al U.S. Pat. No. 4,354,764.

Figure 3:
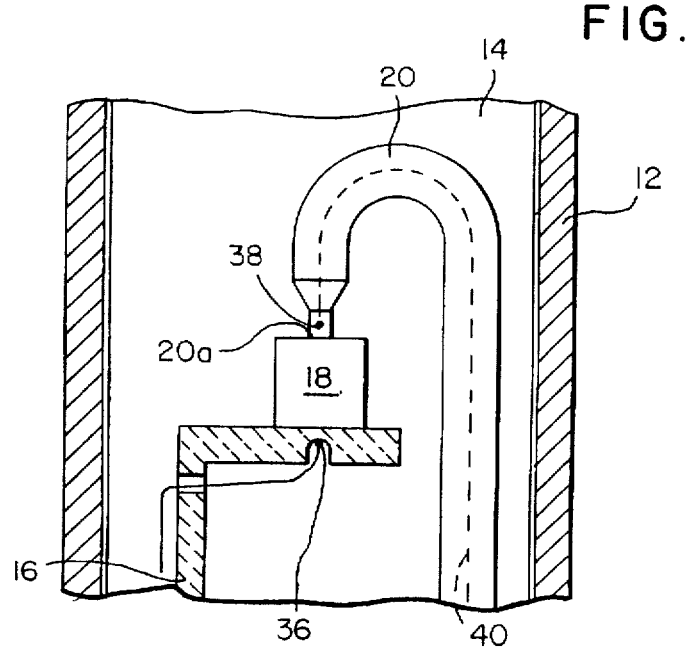
FIG. 3 is a detailed view of the sample support and measuring means of the apparatus of FIG. 2.

FIG. 3 shows a detail of furnace 12 of the instrument according to FIG. 2. Sample 18 rests on sample carrier 16 that, in a recess contained in its bottom surface is arranged temperature sensor 36, so that the sample temperature can be measured in the immediate vicinity of the sample. Measurement sample 20 has a specially shaped measurement surface 20a with which it rests on top of the sample. To improve the accuracy of the measurement of the sample temperature, one may, in the immediate vicinity of this measurement surface 20a, at the tip of the measurement strap 20, arrange another temperature sensor 38 whose measurement value is supplied via line 40 to the temperature control, not shown, so that one can consider temperature differences in furnace compartment 14. The temperature sensor that is required to measure the furnace temperature is not illustrated in this FIG. 3.

While the preferred forms and embodiments have been illustrated and described, it will be apparent that changes may be made without deviating from the inventive concepts set forth above.

What is claimed is:

1. Thermal analysis apparatus for determining the temperature difference between a sample (2) to be measured and a reference value ($T_{Rset}$ (t)), comprising:
   (a) a furnace (1) containing a chamber (10) for receiving a sample the temperature of which is to be measured;
   (b) mathematical model means (46) for producing from a given input set point temperature ($T_{Rset}(t)$) an output set point temperature ($T_{set}$ (t)) in accordance with a proportionality factor $\gamma(T)$ that is a function of temperature;
   (c) means (52) for detecting furnace temperature ($T_O$);
   (d) means (54) for detecting temperature adjacent the sample position ($T_P$);
   (e) means (47) for producing the difference between the temperature adjacent the sample ($T_P$) and said given input set point temperature ($T_{Rset}$ (t)), thereby to produce a single differential temperature analysis (SDTA);
   (f) means including a furnace temperature controller (48) responsive to said furnace temperature ($T_O$) and to said output setpoint ($T_{set}(t)$) for controlling the temperature of said furnace to cause the temperature at the sample position ($T_P$) to correspond generally with said input setpoint temperature ($T_{rset}(t)$); and
   (g) means for measuring a dimensional change (Q) of the sample.

2. Apparatus as defined in claim 1, wherein said proportionality factor $\gamma(T)$ that is described by a regression of a polynomial.

3. Apparatus as defined in claim 2, where said polynomial is of the second order.

4. Apparatus as defined in claim 1, wherein said dimensional change measuring means includes a measurement strap (20) adapted to engage the sample, and differential transformer means (23) for measuring the movement of at least a portion of said measuring strap relative to the sample.

5. Apparatus as defined in claim 1, where said dimensional change measuring means further includes load compensation means (29) including a differential transformer (23).

6. Apparatus as defined in claim 1, wherein said proportionality factor ($\gamma(T)$) for a given literature temperature ($T_{Lit}$) is determined as a function of the difference between furnace temperature ($T_O$) and said literature temperature ($T_{Lit}$) relative to different heating rates ($dT_R/dt$) of the sample.

7. Apparatus as defined in claim 4, and further including sample temperature sensing means (38) mounted on said measurement strap in contact with a surface (20a) of said sample.

8. A method for determining the temperature difference between a sample (2) arranged at a given position in a furnace chamber and a measured reference temperature, comprising:

(a) measuring and storing the temperature ($T_P$) in the chamber adjacent the sample position with the sample removed from the chamber, thereby to obtain a reference temperature ($T_R$);

(b) measuring the temperature ($T_P$) in the chamber adjacent the sample position with the sample arranged in the furnace chamber, thereby to obtain a sample temperature ($T_S$);

(c) obtaining the difference between said sample temperature ($T_S$) and said reference temperature ($T_R$), thereby to produce a single differential temperature analysis (SDTA);

(d) producing from a given setpoint temperature ($T_{Rset}(t)$) an output setpoint temperature ($T_{set}(t)$) in accordance with a proportionality factor $\gamma(T)$ that is a function of temperatures;

(e) detecting furnace temperature ($T_O$);

(f) controlling the temperature of the furnace chamber in accordance with said furnace temperature ($T_O$) and said output setpoint temperature ($T_{set}(t)$); and (g) measuring simultaneously with the furnace temperature controlling step at least one dimensional change (Q) of the sample.

9. A method for determining the temperature difference between a sample (2) in a furnace chamber and a given reference temperature ($T_{Rset}(t)$), comprising:

(a) measuring the temperature ($T_P$) in the chamber adjacent the sample position with the sample arranged in the furnace chamber;

(b) obtaining the difference between said sample temperature ($T_S$) and said given reference temperature ($T_{Rset}(t)$) thereby to produce a single differential temperature (SDTA);

(c) producing from a given setpoint temperature ($T_{Rset}(t)$) an output setpoint temperature ($T_{set}(t)$) in accordance with a proportionality factor $\gamma(T)$ that is a function of temperature;

(d) detecting furnace temperature ($T_O$);

(e) controlling the temperature of the furnace chamber in accordance with said furnace temperature ($T_O$) and said output setpoint temperature ($T_{set}(t)$); and (f) measuring a dimensional change (Q) of the sample.

* * * * *